United States Patent [19]

Bräumer et al.

[11] 4,131,650

[45] Dec. 26, 1978

[54] COLLAGEN FOIL FOR COSMETIC APPLICATION

[75] Inventors: Klaus Bräumer, Weinheim; Zdenek Eckmayer, Heidelberg, both of Germany

[73] Assignee: Firma Carl Freudenberg, Weinheim, Germany

[21] Appl. No.: 675,363

[22] Filed: Apr. 9, 1976

[30] Foreign Application Priority Data

Apr. 19, 1975 [DE] Fed. Rep. of Germany ....... 2517452

[51] Int. Cl.$^2$ .................. A61K 9/70; A01N 5/00; A61F 13/00
[52] U.S. Cl. .................... 424/28; 424/359; 128/DIG. 8
[58] Field of Search .......... 128/DIG. 8, 365; 424/28, 359, 365, 10.5

[56] References Cited

U.S. PATENT DOCUMENTS

| | | | |
|---|---|---|---|
| 3,016,334 | 1/1962 | Lewis | 424/359 |
| 3,628,974 | 2/1970 | Battista | 424/359 |
| 3,803,300 | 4/1974 | Pospischil | 424/28 |
| 3,991,184 | 11/1976 | Kludas et al. | 424/359 |

OTHER PUBLICATIONS

Bria et al., "Collagen and Gelatin and their Use in Cosmetics", Chem. Abst. vol. 79, 1973, p. 139607c.
Kludas et al., "Cosmetic Creams Cont. Sol. Collagen", Chem. Abst., vol. 77, 1972, p. 105523r.

*Primary Examiner*—Henry R. Jiles
*Assistant Examiner*—Cary Owen
*Attorney, Agent, or Firm*—Sprung, Felfe, Horn, Lynch & Kramer

[57] ABSTRACT

In the treatment of skin wherein an aqueous paste is applied to the skin, left in contact therewith for a period of time and thereafter removed, the improvement which comprises placing over the paste a foil containing at least about 3 percent of water soluble collagen by weight and having a water permeability of more than about 0.1 gram/dm$^2$/minute, whereby collagen is transported through the paste and is absorbed by the skin. Desirably the foil is about 0.01 to 0.03 mm thick and is cross-linked to an extent corresponding to that produced by about 0.1-0.5 percent by weight of glutardialdehyde applied in an acid medium. It may further contain a cosmetically active agent such as an amino acid, peptide, protein, hormone, placenta-extract, phosphatide, tissue-extract, fresh cells and vitamins. The paste may be dried by heating, producing shrinkage of the foil to increase contact with the skin.

10 Claims, No Drawings

COLLAGEN FOIL FOR COSMETIC APPLICATION

Cosmetic applications such as packs, masks or the like are known and used for numerous purposes. In general, they consist of pasty substances which are applied to the skin surface to be treated, for instance the face, and contain active substances for the care and conditioning of the skin. The active substances penetrate into the skin either from the paste which retains its consistency, or after some time the paste dries and hardens, and then the active substances develop the desired effect. Different effects of this kind can be achieved individually or in combination, depending on the consistency and composition of the active materials, e.g. greasing and degreasing, curing, soothing, astringent, moistening and dehydrating face packs and masks.

It has been found that the effect of such packs, masks or the like can be increased considerably by covering them with a collagen foil which contains at least about 3 percent by weight of water soluble collagen and exhibits a water permeability of more than about 0.1 gram/dm$^2$/minute. As a result of the use of such a collagen foil, the condition effect is implemented by the water soluble collagen of the foil which penetrates into the mask.

At the same time the collagen foil protects the pack or mask from drying out, but it does not seal it hermetically as the foil remains porous during use. It is suitable to employ a foil which contains water soluble collagen which shrinks when the pack dries on the skin. Thus the pack is always pressed tightly against the skin and it can be pulled off easily after use.

Suitably the collagen foil may contain up to about 10 percent by weight of water soluble collagen. Preferably it is of a uniform thickness of about 0.01 to 0.03 mm.

The foil has a microporous structure so that only small molecules with a molecular weight below about 1000 can diffuse. The collagen is present in uncrosslinked form or in only slightly crosslinked form as can be achieved in known manner by use of approximately 0.1 to 0.5 percent by weight of glutardialdehyde, based on collagen, in the acid range. Preferably the degree of crosslinking corresponds to approximately 0.15 percent by weight of glutardialdehyde. If other crosslinking methods are applied, the degrees of crosslinking of the foil should correspond to these values.

A special effect is realized when there are employed collagen foils which additionally contain uniformly distributed therethrough known cosmetically active effective substances such as suitable amino acids, peptides, proteins, hormones, placenta-extracts, phosphatides, tissue-extracts, fresh cells or vitamins. The active substances can thus always be adapted and selected according to the desired purpose.

The collagen foil can be produced in conventional manner, care being exercised to ensure the desired relatively high content of soluble collagen. Usually in this case an ordinary collagen solution and/or dispersion or a mixture of both is treated with a solution of salt or another chemical agent to precipitate the collagen. After desalination and the application of softening agents, upon drying a collagen material is obtained which may be crosslinked as desired with other additives or treated, for example with impregnation agents, cosmetically active substances, or the like. The material can be manufactured into foils of different thickness.

For the production of collagen foils for cosmetic purposes, the material should contain the indicated proportion of water soluble collagen. For this purpose it is suitable to adjust the pH-value of the material during the production of the foil such that the soluble collagen can easily be extracted after crosslinking and drying. The pH-value of the collagen preparation should in this case be under about 5.0, preferably between about 3.5 and 4.5. Such slightly crosslinked collagen gives good results whereas, however, the best values are achieved with uncrosslinked collagen foils. Uncrosslinked collagen, however, tends to exhibit high swelling and has low wet strength so that slight crosslinking in the acid range is recommendable. For cosmetic purposes, the use of glutardialdehyde is recommended in about 0.1 to 0.5 percent by weight of the collagen.

Desirably the collagen foil is dried at low temperature, i.e. below about 40° C. Otherwise the material becomes brittle and the soluble collagen denatures. When working with known active substances, such as appropriate amino acids, peptides, proteins, hormones, placenta-extracts, phosphatides, tissue-extracts, fresh cells, vitamins or the like, these active substances are bound onto the collagen and, after applying of the foil to the skin, are continuously absorbed by the skin over the whole time of contact.

The following example shows the use of a collagen foil for cosmetic purposes according to the invention.

EXAMPLE

A pack made from an oil-in-water emulsion is applied in the usual manner to the face, leaving only the eye lids and the lips free. The pack is covered uniformly without applying pressure with a damp collagen foil 0.02 mm thick, containing 5 percent of water soluble collagen and having a water permeability of about 0.2 gram/dm$^2$/minute. The foil is dried by means of radiant heat whereby it shrinks and adapts to the surface of the skin without compressing it. At the same time, the pack is absorbed by the skin. During the treatment, the soluble collagen is extracted from the foil and brought to the skin through the pack. After the treatment is carried out, the residual foil is pulled off and the skin is treated further, if desired.

A considerably improved effect is achieved compared to the same pack without use of collagen foil as evidenced by an increased supply of blood, tightening of the skin, and the like.

The foil may comprise a conventional collagen nonwoven fabric, or it may comprise a plastic or textile fabric carrier as a support for the collagen, or it may comprise textile fibers intermingled with collagen fibers, these latter alternatives facilitating subsequent stripping of the foil. The non-absorbable portion of the material consists of insoluble collagen. The cosmetically active agents when present may be distributed through the foil uniformly or in a layer and their content relative to the collagen and/or the foil may vary widely.

It will be appreciated that the instant specification and examples are set forth by way of illustration and not limitation, and that various modifications and changes may be made without departing from the spirit and scope of the present invention.

What is claimed is:

1. In the treatment of skin wherein an aqueous cosmetically-active paste is applied to the skin, left in contact therewith for a period of time and thereafter removed, the improvement which comprises placing over the paste a collagen-foil containing at least about 3 percent of water soluble collagen by weight and having a water permeability of more than about 0.1 gram/dm$^2$/minute, whereby collagen is transported through the paste and is absorbed by the skin.

2. The process according to claim 1, wherein the paste is permitted to dry while in contact with the skin and the collagen foil shrinks during such drying.

3. The process according to claim 1, wherein the foil contains about 5 to 10 percent of water soluble collagen by weight and has a thickness of about 0.01 to 0.03 mm.

4. The process according to claim 1, wherein the collagen in the foil is at most only partially crosslinked.

5. The process according to claim 1, wherein the collagen in the foil is crosslinked to an extent corresponding to that produced by about 0.1–0.5 percent by weight of glutardialdehyde applied in an acid medium.

6. The process according to claim 1, wherein the foil further contains at least one cosmetically active agent selected from the group consisting of an amino acid, peptide, protein, hormone, placenta-extract, phosphatide, tissue-extract, fresh cells and vitamins.

7. The process according to claim 6, wherein the foil contains about 5 to 10 percent of water soluble collagen by weight and has a thickness of about 0.01 to 0.03 mm, the collagen in the foil is crosslinked to an extent corresponding to that produced by about 0.1–0.5 percent by weight of glutardialdehyde applied to an acid medium, the paste is dried while in contact with the skin and the collagen foil shrinks during such drying.

8. A foil suited for cosmetic use containing about 3 to 10 percent by weight of water soluble collagen, having a thickness of about 0.01 to 0.03 mm and a water permeability of more than about 0.1 gram/dm$^2$/minute.

9. A foil according to claim 8 crosslinked to an extent corresponding to that produced by about 0.1–0.5 percent by weight of glutardialdehyde applied in an acid medium.

10. A foil according to claim 9 further containing at least one cosmetically active agent selected from the group consisting of an amino acid, peptide, protein, hormone, placenta-extract, phosphatide, tissue-extract, fresh cells and vitamins.

* * * * *